United States Patent
Li et al.

(10) Patent No.: US 11,733,153 B1
(45) Date of Patent: Aug. 22, 2023

(54) METHOD FOR EVALUATING ENVIRONMENTAL EROSION OF THAUMASITE IN TUNNEL CONCRETE

(71) Applicant: RESEARCH INSTITUTE OF HIGHWAY MINISTRY OF TRANSPORT, Beijing (CN)

(72) Inventors: Xuefeng Li, Beijing (CN); Hualao Wang, Beijing (CN)

(73) Assignee: RESEARCH INSTITUTE OF HIGHWAY MINISTRY OF TRANSPORT, Beijing (CN)

( * ) Notice: Subject to any disclaimer, the term of this patent is extended or adjusted under 35 U.S.C. 154(b) by 0 days.

(21) Appl. No.: 18/175,150

(22) Filed: Feb. 27, 2023

(30) Foreign Application Priority Data

Sep. 1, 2022 (CN) .......................... 202211059428.4

(51) Int. Cl.
*G01N 17/00* (2006.01)
*G01N 33/38* (2006.01)
*G01N 33/18* (2006.01)

(52) U.S. Cl.
CPC ......... *G01N 17/00* (2013.01); *G01N 33/1846* (2013.01); *G01N 33/383* (2013.01)

(58) Field of Classification Search
CPC ........... G01N 33/1826; G01N 33/1846; G01N 33/38; G01N 33/383; G01N 17/00; Y10T 436/18; Y10T 436/204998
USPC ........................ 436/2, 5, 6, 72, 79, 119, 133
See application file for complete search history.

(56) References Cited

U.S. PATENT DOCUMENTS

2023/0129027 A1* 4/2023 Xu ...................... C04B 24/2641
524/2

FOREIGN PATENT DOCUMENTS

| CN | 108562529 A | | 9/2018 |
|---|---|---|---|
| CN | 110567513 A | | 12/2019 |
| CN | 111693447 A | | 9/2020 |
| CN | 111948337 A | | 11/2020 |
| CN | 113310882 A | * | 8/2021 |
| CN | 113588528 A | | 11/2021 |
| CN | 113860819 A | * | 12/2021 |

OTHER PUBLICATIONS

Kun-Lin et al. J. Cent. South Univ., vol. 19, 2012, pp. 2340-2347.*
Hobbs, D.W. Cement and Concrete Composites, vol. 25, 2003, pp. 1195-1202.*
Wei, "An Evaluation and Analysis on chemical corrosion of water and soil to concrete Publication name:Construction Materials & Decoration" 2018, Issue: No. 10.

* cited by examiner

*Primary Examiner* — Maureen Wallenhorst
(74) *Attorney, Agent, or Firm* — Stuart H. Mayer; Mayer & Williams PC

(57) ABSTRACT

Disclosed is a method for evaluating environmental erosion of thaumasite in tunnel concrete, including: acquiring natural corrosion action parameters and environmental influence action parameters, and evaluating a natural corrosion situation based on the natural corrosion action parameters to obtain an initial evaluation result; and modifying the initial evaluation result based on the environmental influence action parameters to obtain a target evaluation result.

4 Claims, 2 Drawing Sheets

METHOD FOR EVALUATING ENVIRONMENTAL EROSION OF THAUMASITE IN TUNNEL CONCRETE

CROSS-REFERENCE TO RELATED APPLICATIONS

This application claims priority to Chinese Patent Application No. 202211059428.4, filed on Sep. 1, 2022, the contents of which are hereby incorporated by reference.

TECHNICAL FIELD

The application belongs to the technical field of erosion evaluation, and in particular relates to a method for evaluating environmental erosion of thaumasite in tunnel concrete.

BACKGROUND

Thaumasite sulfate attack (TSA) is a specific type of concrete sulfate attack that occurs at low temperatures (usually below 15 degree Celsius (° C.)) when both sulfate and carbonate ions are present in the concrete or in the environment. Under the conditions of TSA, the bonding material of concrete, calcium silicate hydrate (C-S-H), is directly muddied, and the eroded material has a similar x-ray diffraction (XRD) pattern to calcium alumina, so the TSA is often misidentified as common sulfate attack and therefore causes great damage. The TSA is currently the most frequently occurring type of erosion of concrete in tunnel structures due to the direct contact between the concrete of the initial support structure and the underground geotechnical body, where the concrete is highly susceptible to reaction with the harmful ions abounded in the groundwater. With the wide distribution of limestone in China, limestone aggregates are used in large quantities in the concrete of tunnel structures, along with the massive application of limestone powder as concrete admixture in cement, so TSA of tunnel structure concrete occurs once the ground temperature is below 15° C.

Presently, an assessment of the environmental action level based on the concentrations of sulfate ions in groundwater is required before designing the durability against sulfate for tunnel structure concrete, with reference to the criteria of sulfate environmental action levels provided in the *Standard for Design of Concrete Structure Durability* (GB/T 50476-2019); yet, extensive engineering cases have demonstrated that this table, as being used for evaluating the sulfate attack rating of concrete in tunnel structures, still has the following problems:

firstly, the effectiveness of dry and wet cycles on the concrete waterfront of the tunnel structure is underestimated; as evidenced by a considerable number of engineering cases, given that the development of fissures in the surrounding rocks results in strong surface-underground connectivity, significant wet and dry cycling is likely to occur even if the climate of the tunnel site is semi-arid, resulting in an increase (up to tens of times) in the concentration of sulfate ions in the groundwater; consequently, the assessment of the environmental action level of sulfate erosion according to the measured sulfate ion concentrations in groundwater tends to underestimate the erosive effect of sulfate ions on concrete, which ultimately leads to inadequate design of the durability of tunnel structure concrete against sulfate erosion; secondly, existing environmental action levels for sulfate erosion do not take into account temperature effects, and thus cannot be used to assess the sulfate erosion environment of thaumasite; and finally, for deeply buried tunnel structures, it is difficult to propose a method to determine the wet and dry cycle effect of the surrounding rocks more accurately due to their underground structure.

SUMMARY

In order to solve the above problems, the present application provides the following technical schemes: a method for evaluating environmental erosion of thaumasite in tunnel concrete, including:

acquiring natural corrosion action parameters and environmental influence action parameters, and evaluating a natural corrosion situation based on the natural corrosion action parameters to obtain an initial evaluation result; and modifying the initial evaluation result based on the environmental influence action parameters to obtain a target evaluation result.

Optionally, the natural corrosion action parameters include sulfate ion concentrations in groundwater, magnesium ion concentrations in groundwater and corrosive carbon dioxide concentrations.

Optionally, a process of evaluating a natural corrosion situation based on the natural corrosion action parameters to obtain an initial evaluation result includes:

presetting a natural corrosion action rating scale, and determining a corresponding initial natural corrosion action level based on the natural corrosion action rating scale and the sulfate ion concentrations in groundwater;

determining whether the groundwater contains magnesium ions and corrosive carbon dioxide, and if not, directly evaluating the natural corrosion situation based on the sulfate ion concentrations to obtain the initial evaluation result;

otherwise, correcting the initial natural corrosion action level based on the magnesium ion concentrations and the corrosive carbon dioxide concentrations in the groundwater to obtain a target natural corrosion action level; and evaluating the natural corrosion situation based on the target natural corrosion action level to obtain the initial evaluation result.

Optionally, the environmental influence action parameters include degrees of water-richness of tunnel surrounding rocks, degrees of connectivity between surrounding rocks and an atmosphere, degrees of vapor evaporation from surface water in a tunnel site, and ambient temperatures in the tunnel site;

the degrees of water-richness of tunnel surrounding rocks are used to characterize the surrounding rocks for water content, including dryness of the surrounding rocks, wetness of the surrounding rocks, seepage of the surrounding rocks and water surges of surrounding rocks;

the degrees of connectivity between surrounding rocks and an atmosphere involve strong connectivity, medium connectivity, and weak connectivity; and the degrees of vapor evaporation from surface water in a tunnel site are divided into arid and humid areas, semi-arid areas, and arid areas based on a climate dryness coefficient K of the tunnel site.

Optionally, the degrees of water-richness of tunnel surrounding rocks are determined by a subsurface runoff module M, with an expression as follows:

$$M = \frac{Q'}{F},$$

where M—subsurface runoff module, in cubic meters per day per square kilometer (m³/(d·km²));

Q'—stream flow or descending spring flow (m³/d) of groundwater recharge, calculated by a flow in dry season; and F—surface drainage area (km²) equivalent to the stream flow or descending spring flow Q'.

Optionally, the climate dryness coefficient is obtained according to an expression as follows:

$$K = \frac{0.16\sum t}{\gamma},$$

where $\Sigma^t$ is an annual accumulated temperature (° C.) during a stable period of daily average temperature ≥10° C., and γ is an annual precipitation (milliliter, mm) during a stable period of average daily temperature ≥10° C.

Optionally, a process of modifying the initial evaluation result based on the environmental influence action parameters to obtain a target evaluation result includes:

determining whether a degree of water-richness of tunnel surrounding rocks is the dryness of the surrounding rocks, if so, directly obtaining an evaluation result of the environmental erosion of thaumasite in tunnel concrete; otherwise, obtaining action levels of environmental dry and wet cycles in the tunnel site based on the degrees of connectivity between surrounding rocks and the atmosphere as well as the degrees of vapor evaporation from surface water in the tunnel site, and correcting the initial evaluation result using the degrees of water-richness of tunnel surrounding rocks, action levels of environmental dry and wet cycles, and ambient temperatures in the tunnel site, thus obtaining the target evaluation result.

The present application discloses the following technical effects:

the method for evaluating environmental erosion of thaumasite in tunnel concrete provided by the present application allows a relatively accurate assessment of the level of humidity and the degree of dry and wet cycles in the tunnel surrounding rocks while considering the temperature effect on the thaumasite erosion, thereby realizing a reliable and reasonable evaluation of the actual thaumasite erosion environment when the tunnel structure concrete is in service; also, the method is technically feasible and operable, with mature techniques for obtaining the values of each evaluation index, and holds a promising prospect for promotion and application.

BRIEF DESCRIPTION OF THE DRAWINGS

For a clearer description of the technical schemes in the embodiments or prior art of the present application, the following drawings are briefly described for use in the embodiments, and it is obvious that the drawings in the following description are only some embodiments of the present application, and that other drawings are available to those of ordinary skill in the art without creative efforts.

DETAILED DESCRIPTION OF THE EMBODIMENTS

The technical schemes in the embodiments of the present application are described clearly and comprehensively below in conjunction with the accompanying drawings in the embodiments of the present application, and it is clear that the described embodiments are only a part of the embodiments of the present application, not all of them. Based on the embodiments in the present application, all other embodiments obtained by a person of ordinary skill in the art without making creative labor fall within the scope of protection of the present application.

In order to make the above-mentioned objectives, features and advantages of the present application more obvious and understandable, the following is a further detailed description of the present application together with the accompanying drawings and specific embodiments.

Figure 1:
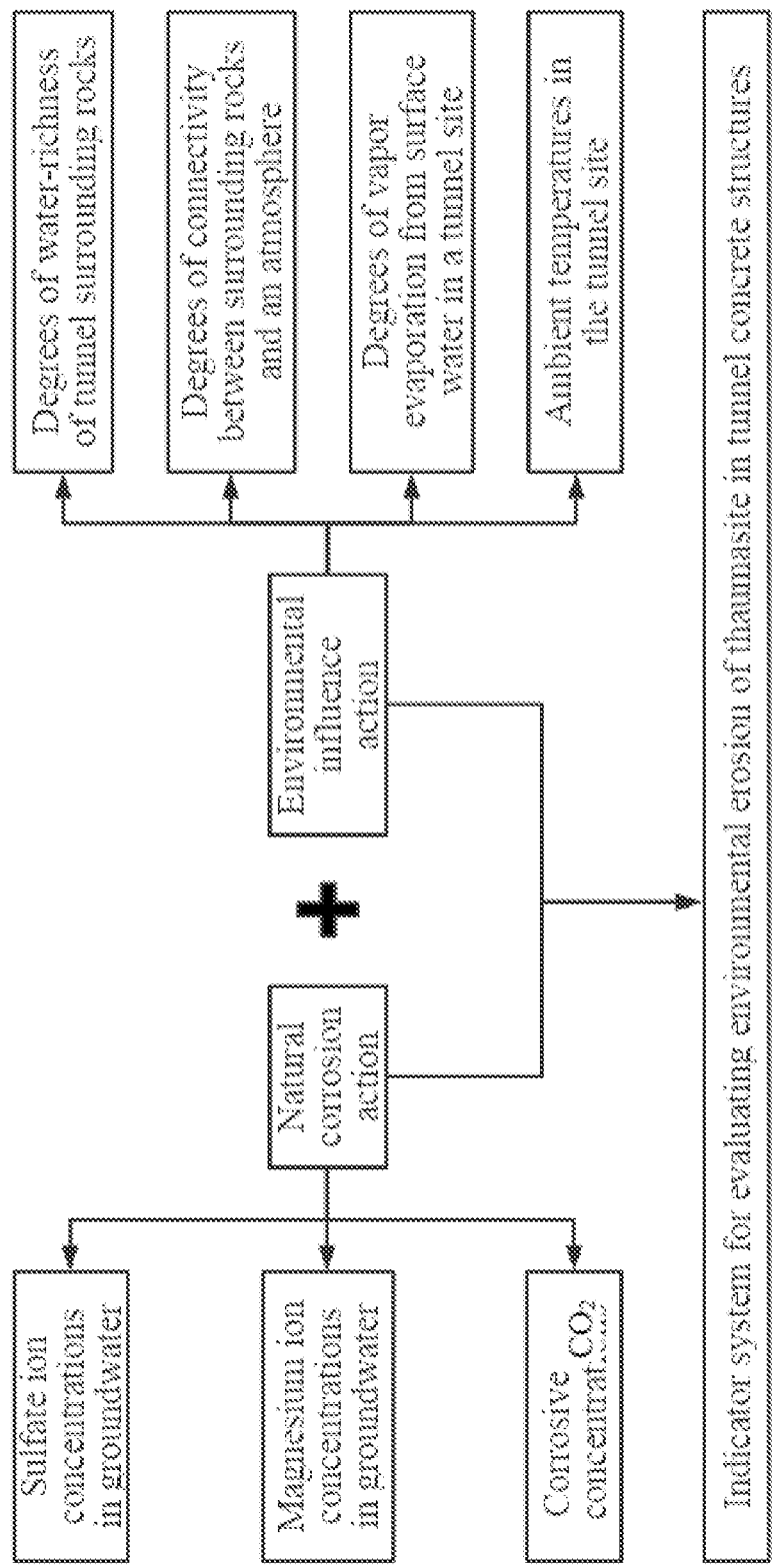
FIG. 1 shows a schematic diagram of an evaluation parameter system according to an embodiment of the present application.

As shown in FIG. 1, the present application provides a method for evaluating environmental erosion of thaumasite in tunnel concrete, including:

an indicator system of evaluation parameters, including natural corrosion action indicator parameters and environmental influence action indicator parameters, is obtained, where the natural corrosion action indicator parameters are used to evaluate natural corrosion grades of sulfate ions in groundwater, and the environmental influence action indicator parameters are used to evaluate a dry and wet cyclic effect of surrounding rocks in contact with a tunnel lining structure and temperature effect levels in a tunnel site.

The natural corrosion action indicator parameters include sulfate ion concentrations in groundwater, magnesium ion concentrations in groundwater and corrosive carbon dioxide concentrations.

There are 5 levels of natural corrosion action, namely SL-1, SL-2, SL-3, SL-4 and SL-5, and the specific determination is as follows: firstly, the natural corrosion action levels are preliminarily determined according to the measured sulfate ion concentrations in the groundwater illustrates in Table 1, and then the preliminarily determined natural corrosion action levels are revised according to the magnesium ion concentrations and corrosive carbon dioxide concentrations in the groundwater listed in Table 2. In case of inconsistency between the two revised levels, the one with the higher revised levels shall prevail.

TABLE 1

| Action grade | Sulfate ion concentrations in groundwater (mg/L) |
|---|---|
| SL-1 | ≤400 |
| SL-2 | (400, 1,400] |
| SL-3 | (1,400, 3,000] |
| SL-4 | (3,000, 6,000] |
| SL-5 | >6,000 |

TABLE 2

| Action level correction | Magnesium ion content in groundwater (mg/L) | Corrosive carbon dioxide concentrations in groundwater (mg/L) |
|---|---|---|
| No change | ≤1,000 | ≤40 |
| Increased by 1 level | (1,000, 3,000] | (40, 100] |
| Increased by 2 levels | >3,000 | >100 |

The environmental influence action indicator parameters include degrees of water-richness of tunnel surrounding rocks, degrees of connectivity between surrounding rocks and an atmosphere, degrees of vapor evaporation from surface water in the tunnel site, and ambient temperatures in the tunnel site.

Among them, the degrees of water-richness of tunnel surrounding rocks are used to characterize the surrounding rocks for water content, and are determined according to a subsurface runoff module M, including dryness of the surrounding rocks, wetness of the surrounding rocks, seepage of the surrounding rocks and water surges of surrounding rocks; the specific criteria are shown in Table 3, and the calculation method is shown in Expression (1):

TABLE 3

| Dryness of surrounding rocks | Wetness of surrounding rocks | Seepage of surrounding rocks | Water surges of surrounding rocks |
|---|---|---|---|
| M < 100 | 100 ≤ M < 1,000 | 1,000 ≤ M < 3,000 | M ≥ 3,000 |

$$M = \frac{Q'}{F}, \quad (1)$$

where M—subsurface runoff module, in cubic meters per day per square kilometer (m³/(d·km²));
Q'—stream flow or descending spring flow (m³/d) of groundwater recharge, calculated by a flow in a dry season; and
F—surface drainage area (km²) equivalent to the stream flow or descending spring flow Q'.

The degrees of connectivity between surrounding rocks and an atmosphere are classified into 3 levels of strong connectivity, medium connectivity, and weak connectivity according to the development of the surrounding rocks given in the geological survey of the tunnel, and the determination criteria are shown in Table 4.

TABLE 4

| Degrees of connectivity | Development degree of fractured strata | Karst development degree in karst area |
|---|---|---|
| Weak connectivity | Weak development | Weak development |
| Medium connectivity | Medium development | Medium development |
| Strong connectivity | Strong development | |

The degrees of vapor evaporation from surface water in the tunnel site are divided into arid and humid areas, semi-arid areas, and arid areas based on a climate dryness coefficient K of the tunnel site, with specific division criteria as shown in Table 5, and the K value is obtained by Expression (2):

TABLE 5

| Arid and humid area | Semi-arid area | Arid area |
|---|---|---|
| K < 1.5 | 1.5 ≤ K < 4.0 | 4.0 ≤ K |

$$K = \frac{0.16 \sum t}{\gamma}, \quad (2)$$

where $\Sigma t$—an annual accumulated temperature (degree Celsius, °C.) during a stable period of daily average temperature ≥10° C.; and
γ—an annual precipitation (milliliter, mm) during a stable period of average daily temperature ≥10° C.

The degrees of connectivity between surrounding rocks and an atmosphere and the degrees of vapor evaporation from surface water in the tunnel site combine to develop the action levels of environmental dry and wet cycles in the tunnel site is shown in Table 6.

TABLE 6

| Action levels of dry and wet cycles | Degrees of connectivity between surrounding rock and atmosphere | Degrees of vapor evaporation from surface water |
|---|---|---|
| Grade I | Weak connectivity | Arid and humid area, semi-arid area, arid area |
| Grade I | Medium or strong connectivity | Arid and humid area |
| Grade II | Medium connectivity | Semi-arid area |
| Grade II | Strong connectivity | Semi-arid area |
| Grade III | Strong connectivity | Arid area |

The ambient temperature of the tunnel site is measured by the local annual average temperature T (° C.), and the temperature is divided into 3 impact levels at 5° C. intervals shown in Table 7.

TABLE 7

| Action grade | Local annual average temperature T (° C.) |
|---|---|
| Grade I | 10° C. < T ≤ 15° C. |
| Grade II | 5° C. < T ≤ 10° C. |
| Grade III | ≤5° C. |

Figure 2:
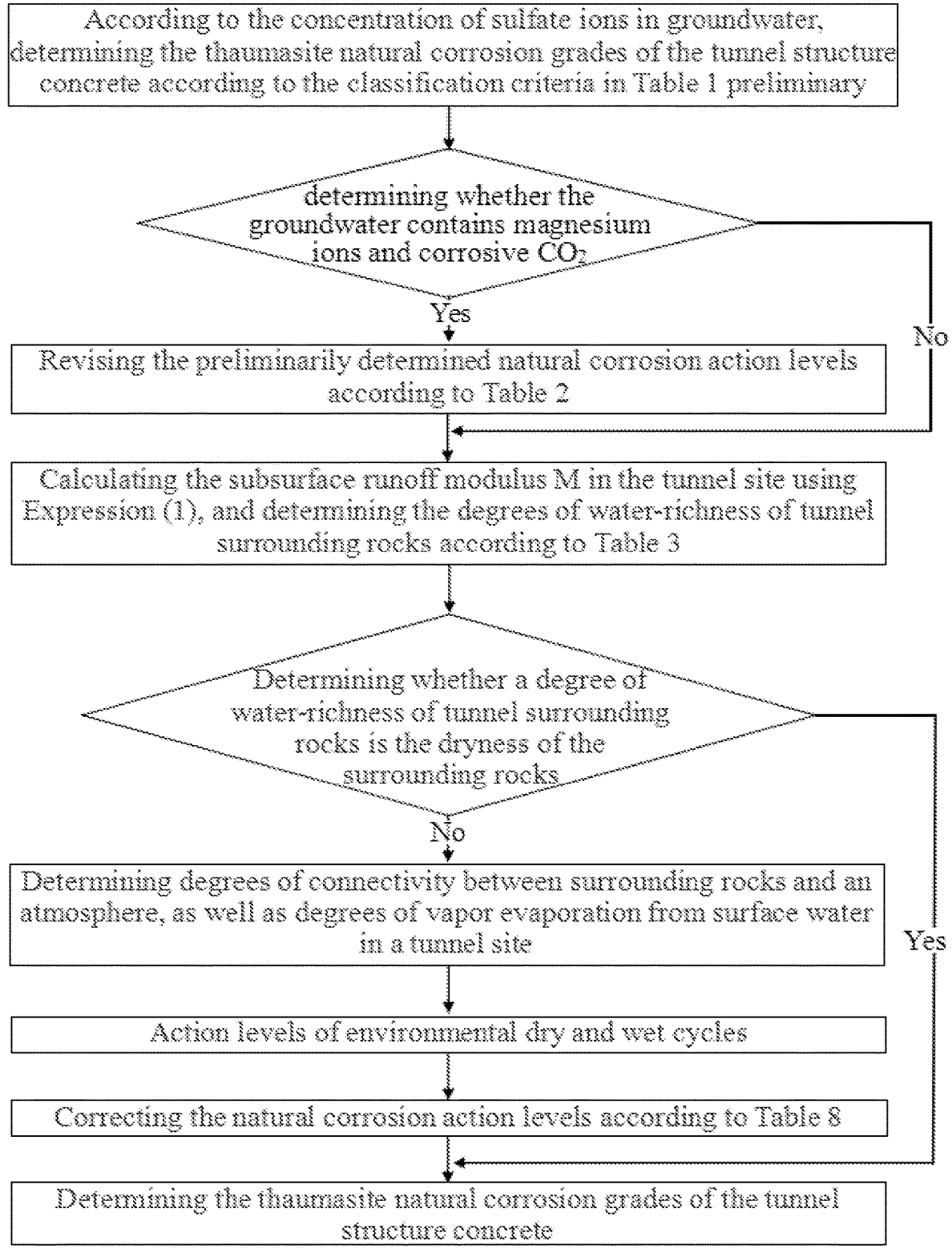
FIG. 2 is a flowchart illustrating an evaluation method according to an embodiment of the present application.

As revising the natural corrosion action levels, an order of judging the degrees of water-richness of tunnel surrounding rocks first, then determining the action levels of dry and wet cycles, and considering the ambient temperature of the tunnel site, and finally determining a correction level of the natural corrosion action levels in accordance with the Table 8; during the correction process, the levels are increased by at most 3 levels, and the corrected levels do not exceed the level of SL-5. The corrected levels are the final environmental erosion levels of thaumasite in tunnel structure concrete, see FIG. 2 for the flow chart.

TABLE 8

| Degrees of water-richness of surrounding rocks | Action levels of dry and wet cycles | Ambient temperature of tunnel site | Correction of natural corrosion action level |
|---|---|---|---|
| Dryness of surrounding rocks | Grades I, II and III | Grades I, II and III | Unchanged |

TABLE 8-continued

| Degrees of water-richness of surrounding rocks | Action levels of dry and wet cycles | Ambient temperature of tunnel site | Correction of natural corrosion action level |
|---|---|---|---|
| Wetness of surrounding rocks | Grades I and II | Grades I, II and III | Unchanged |
| Wetness of surrounding rocks | Grade III | Grades I, II and III | Increased by 1 level |
| Seepage of surrounding rocks | Grade I | Grades I, II and III | Unchanged |
| Seepage of surrounding rocks | Grades II and III | Grades I and II | Increased by 1 level |
| Seepage of surrounding rocks | Grades II and III | Grade III | Increased by 2 levels |
| Water surges of surrounding rocks | Grade I | Grades I, II and III | Increased by 1 level |
| Water surges of surrounding rocks | Grade II | Grades I, II and III | Increased by 2 levels |
| Water surges of surrounding rocks | Grade III | Grade III | Increased by 3 levels |

According to the present application, the natural corrosion action levels are determined firstly using sulfate ions in groundwater, then the preliminarily determined natural corrosion action levels are corrected based on the concentrations of magnesium ions and corrosive carbon dioxide to comprehensively determine the natural corrosion action levels; on this basis, the impact of environmental influence action indicator parameters is considered, and the influence degrees of dry and wet cyclic effect of tunnel surrounding rocks and temperature effect are considered comprehensively based on the degrees of water-richness of tunnel surrounding rocks, the degrees of connectivity between surrounding rocks and an atmosphere, the degrees of vapor evaporation from surface water in the tunnel site and the ambient temperature of the tunnel site, then the natural corrosion action levels are corrected to finally obtain the evaluation result of tunnel structure concrete thaumasite erosion environment.

The above-mentioned embodiments only describe the preferred mode of the present application, and do not limit the scope of the present application. Under the premise of not departing from the design spirit of the present application, various modifications and improvements made by ordinary technicians in the art to the technical scheme of the present application shall fall within the protection scope determined by the claims of the present application.

What is claimed is:

1. A method for evaluating environmental erosion of thaumasite in tunnel concrete, comprising:
acquiring natural corrosion action parameters and environmental influence action parameters, and evaluating a natural corrosion situation based on the natural corrosion action parameters to obtain an initial evaluation result; and modifying the initial evaluation result based on the environmental influence action parameters to obtain a target evaluation result;
wherein a process of evaluating a natural corrosion situation based on the natural corrosion action parameters to obtain an initial evaluation result comprises:
presetting a natural corrosion action rating scale, and determining a corresponding initial natural corrosion action level based on the natural corrosion action rating scale and sulfate ion concentrations in groundwater;
determining whether the groundwater contains concentrations of magnesium ions and corrosive carbon dioxide, and if not, directly evaluating the natural corrosion situation based on the sulfate ion concentrations to obtain the initial evaluation result;
otherwise, correcting the initial natural corrosion action level based on the magnesium ion concentrations and the corrosive carbon dioxide concentrations in the groundwater to obtain a target natural corrosion action level; and
evaluating the natural corrosion situation based on the target natural corrosion action level to obtain the initial evaluation result;
the environmental influence action parameters comprise degrees of water-richness of tunnel surrounding rocks, degrees of connectivity between the surrounding rocks and an atmosphere, degrees of vapor evaporation from surface water in a tunnel site, and ambient temperatures in the tunnel site;
the degrees of the water-richness of the tunnel surrounding rocks are used to characterize the surrounding rocks for a water content, comprising dryness of the surrounding rocks, wetness of the surrounding rocks, seepage of the surrounding rocks and water surges of the surrounding rocks;
the degrees of the connectivity between surrounding rocks and the atmosphere involve strong connectivity, medium connectivity, and weak connectivity;
the degrees of vapor evaporation from the surface water in the tunnel site is evaluated as arid and humid areas, semi-arid areas and arid areas respectively based on a climate dryness coefficient K of the tunnel site; and
a process of modifying the initial evaluation result based on the environmental influence action parameters to obtain a target evaluation result comprises:
determining whether a degree of the water-richness of the tunnel surrounding rocks is the dryness of the surrounding rocks, if so, directly obtaining an evaluation result of the environmental erosion of the thaumasite in the tunnel concrete; otherwise, obtaining action levels of environmental dry and wet cycles in the tunnel site based on the degrees of connectivity between the surrounding rocks and the atmosphere as well as the degrees of vapor evaporation from the surface water in the tunnel site, and correcting the initial evaluation result using the degrees of water-richness of the tunnel surrounding rocks, action levels of environmental dry and wet cycles, and ambient temperatures in the tunnel site, and obtaining the target evaluation result.

2. The method for evaluating environmental erosion of thaumasite in tunnel concrete according to claim 1, wherein the natural corrosion action parameters comprise the sulfate ion concentrations in the groundwater, the magnesium ion concentrations in the groundwater and the corrosive carbon dioxide concentrations.

3. The method for evaluating environmental erosion of thaumasite in tunnel concrete according to claim 1, wherein the degrees of the water-richness of the tunnel surrounding rocks are determined by a subsurface runoff module M with an expression below:

$$M = \frac{Q'}{F},$$

wherein M—a subsurface runoff module, in cubic meters per day per square kilometer (m³/(d·km²));

Q'—stream flow or descending spring flow (m³/d) of groundwater recharge, calculated by a flow in dry season; and F—surface drainage area (km²) equivalent to the stream flow or descending spring flow Q'.

4. The method for evaluating environmental erosion of thaumasite in tunnel concrete according to claim 1, wherein the climate dryness coefficient is obtained according to an expression below:

$$K = \frac{0.16 \sum t}{\gamma},$$

wherein $\Sigma^t$ is an annual accumulated temperature (° C.) during a stable period of a daily mean temperature ≥10° C., and γ is an annual precipitation in milliliter, mm during a stable period of a daily mean temperature ≥10° C.

\* \* \* \* \*